(12) United States Patent
Carniato et al.

(10) Patent No.: US 6,339,082 B1
(45) Date of Patent: Jan. 15, 2002

(54) TRICYCLIC COMPOUNDS, PREPARATION METHOD AND SAID METHOD INTERMEDIATES, APPLICATION AS MEDICINES AND PHARMACEUTICAL COMPOSITIONS CONTAINING SAME

(75) Inventors: Denis Carniato, Cagnes sur Mer (FR); Thomas R. Gadek, Oakland, CA (US); Jean-Francois Gourvest, Claye-Souilly (FR); Jochen Knolle, Kriftel (DE); Robert S. McDowell, San Francisco, CA (US); Anurschirwan Peyman, Kelkheim (DE)

(73) Assignees: Aventis Pharma S.A. (FR); Genetech, Inc.

( * ) Notice: Subject to any disclaimer, the term of this patent is extended or adjusted under 35 U.S.C. 154(b) by 0 days.

(21) Appl. No.: 09/509,327

(22) PCT Filed: Sep. 23, 1998

(86) PCT No.: PCT/FR98/02038

§ 371 Date: Jun. 29, 2000

§ 102(e) Date: Jun. 29, 2000

(87) PCT Pub. No.: WO99/15506

PCT Pub. Date: Apr. 1, 1999

(30) Foreign Application Priority Data

Sep. 24, 1997 (FR) ............................................. 97 11858

(51) Int. Cl.⁷ .................... C07D 233/52; C07D 401/12; C07C 69/76; A61K 31/415; A61P 19/10
(52) U.S. Cl. ........................ 514/218; 514/272; 514/275; 514/303; 514/392; 514/393; 514/395; 514/398; 514/510; 514/569; 514/616; 514/621; 514/632; 514/634; 540/492; 540/553; 544/317; 544/332; 546/118; 548/307.4; 548/302.7; 548/321.5; 560/61; 562/461; 564/155; 564/169; 564/251
(58) Field of Search ................................ 514/218, 272, 514/275, 303, 392, 395, 398, 510, 569, 616, 621, 632, 634; 540/492, 553; 544/317, 332; 548/307.4, 302.7, 321.5; 560/61; 562/461; 564/155, 169, 251; 546/118

(56) References Cited

U.S. PATENT DOCUMENTS 6,221,907 B1 * 4/2001 Bernard et al. ............. 514/510

FOREIGN PATENT DOCUMENTS

| EP | 0729933 | 9/1996 |
|----|---------|--------|
| FR | 2446285 | 8/1980 |
| JP | 425537  | 9/1967 |
| WO | 8808842 | 11/1988 |
| WO | 9606087 | 2/1996 |
| WO | 9734865 | 9/1997 |

* cited by examiner

Primary Examiner—Mukund J. Shah
Assistant Examiner—Thomas C McKenzie
(74) Attorney, Agent, or Firm—Bierman, Muserlian and Lucas

(57) ABSTRACT

A compound selected from the group consisting of a compound of the formula

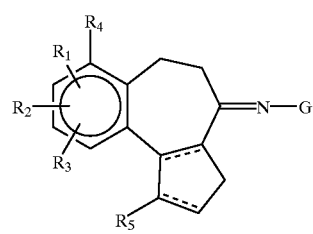

I wherein the substituents are defined as set forth in the specification and its salts with non-toxic pharmaceutically acceptable acids and bases useful for treating loss of bone matrix.

20 Claims, No Drawings

TRICYCLIC COMPOUNDS, PREPARATION METHOD AND SAID METHOD INTERMEDIATES, APPLICATION AS MEDICINES AND PHARMACEUTICAL COMPOSITIONS CONTAINING SAME

This application is a 371 of PCT/FR98/02038 filed Sep. 20, 1998.

The present invention relates to novel tricyclic compounds, their preparation process and the intermediates of this process, their use as medicaments and the pharmaceutical compositions containing them.

A subject of the present invention is the compounds of general formula (I):

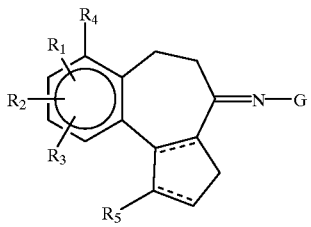

(I)

in which $R_1$ represents a —CONH—[A]—[B]—$COR_6$ group, —[A]— representing a divalent radical derived from an acyclic, linear or branched saturated or unsaturated hydrocarbon, comprising 1 to 12 carbon atoms, substituted by the (Z) group or non substituted,

[B] representing a phenyl radical, a CH(Z) radical, or a single bond, (Z) represents a hydrogen atom, a $(D)_{0-6}$—NRaRb, $(D)_{0-6}$—NH—$SO_2$—Rc, $(D)_{0-6}$—NH—$CO_2$—Rc, $(D)_{0-6}$—NH—CO—Rc, $(D)_{0-6}$—NH—$SO_2$—NH—Rc, $(D)_{0-6}$—NH—CO—NH—Rc, $(D)_{0-6}$—$CO_2$—RC, $(D)_{0-6}$—$SO_2$—Rc, $(D)_{0-6}$—CO-Rc or $(D)_{0-6}$—Rc group in which $(D)_{0-6}$ is a divalent radical derived from an acyclic, linear or branched, saturated or unsaturated hydrocarbon, comprising 0 to 6 carbon atoms, Ra, Rb and Rc represent a hydrogen atom, a $(CH_2)_{0-3}$—Ar radical in which Ar represents a carbocyclic aryl group containing 6 to 18 carbon atoms, a $(CH_2)_{0-3}$—Het radical in which Het represents a radical derived from an aromatic or non aromatic, saturated or non saturated heterocycle, comprising 1 to 9 carbon atoms and 1 to 5 heteroatoms chosen from oxygen, nitrogen or sulphur atoms, a $(CH_2)_{0-3}$—Alk radical in which Alk represents a radical derived from a non aromatic, linear, branched or cyclic, saturated or unsaturated hydrocarbon, and comprising 1 to 12 carbon atoms, the Het, Ar and Alk radicals being able to be non substituted or substituted, or, Ra and Rb represent together with the nitrogen atom to which they are linked a nitrogenous, aromatic or non aromatic, saturated or unsaturated heterocycle, optionally containing one or more heteroatoms chosen from oxygen, nitrogen or sulphur atoms, this radical being able to be substituted or non substituted, $R_6$ represents a hydroxyl radical, an O—Alk, O—Ar, $NH_2$, NH—Alk, $N(Alk)_2$ radical or the remainder of an L or D amino acid, Alk and Ar being as defined previously and being able to be substituted or non substituted, $R_2$ and $R_3$ identical or different represent either a hydrogen atom, a hydroxyl radical, an O—Alk radical or an O—$(CH_2)_{0-3}$—Ar radical, Alk and Ar being as defined previously, or $R_2$ and $R_3$ form together a ring of the —O—$(CRdRe)_n$—O— type, n being an integer from 1 to 5, Rd and Re independently of one another represent a hydrogen atom, an alkyl radical containing 1 to 6 carbon atoms, or a phenyl radical, $R_4$ represents a hydrogen atom, a halogen atom, a hydroxyl, amino, nitro, cyano, $CF_3$, acyl or acyloxy group containing 1 to 12 carbon atoms alkyl, alkenyl, alkynyl, alkylthio, alkoxy, alkylamino, dialkylamino, dialkylaminoalkyl, dialkylaminoalkyloxy group, in which the alkyl term contains 1 to 6 carbon atoms, $R_5$ represents a hydrogen atom, a hydroxyl radical, a halogen atom, an O—Alk radical or an O—$(CH_2)_{0-3}$—Ar radical, Alk and Ar being as defined previously, G represents,
either a radical of formula G1

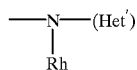

in which Rh is a hydrogen atom or an (Alk) group as defined previously and (Het') is a heterocycle of general formula:

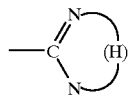

in which (H) forms, with the N═C—NH— unit, the remainder of an aromatic or non aromatic, mono or bicyclic, saturated or non saturated heterocycle comprising 1 to 9 carbon atoms and 2 to 5 heteroatoms chosen from oxygen, nitrogen and sulphur atoms, this radical being able to be substituted or non substituted, or an NRaRb radical (radical G2), Ra and Rb being as defined above, or a (Het) radical (radical G3) as defined above, or an —NRh—C(═X)—NHRc radical (radical G4), in which X is a sulphur, oxygen or NH atom, Rh and Rc are as defined previously, or an —NRh—$SO_2$Rc radical, (radical G5), in which Rh and Rc are as defined previously, the dotted lines represent an optional second bond, as well as the addition salts with acids, bases and esters, $R_1$, $R_2$ and $R_3$ can be in position 8, 9 or 10 of the tricycle.

By compound of formula (I) is meant all the possible geometric isomers and stereoisomers taken individually or in a mixture.

When —[A]— represents a divalent radical derived from an acyclic, linear or branched, saturated or unsaturated, hydrocarbon comprising 1 to 12 carbon atoms, the alkylene radicals of formula —$(CH_2)_n$—, in which n represents an integer comprised between 1 and 12, such as —$CH_2$—, —$CH_2CH_2$—, —$CH_2CH_2CH_2$— or —$CH_2CH_2CH_2CH_2$—, or the alkenylene or alkynylene radicals such as —CH═CH—$CH_2$— or —C≡C—$CH_2$— are designated in particular.

When these divalent radicals are branched, it can be radicals such as —CH($CH_3$)—, —C(Me)$_2$, —$CH_2$—C(Me)$_2$—, —CH(Et)—, —CH(C≡CH)— or —C(C≡CH)(Et)—.

When [B] represents a divalent radical —Ph—, the $COR_6$ group can be in ortho, meta or para position. It is preferably found in para position.

When $(D)_{0-6}$ is a divalent radical derived from an acyclic, linear or branched, saturated or unsaturated, hydrocarbon comprising 0 to 6 carbon atoms, $(D)_{0-6}$ is chosen from the values of [A] mentioned above. By $(D)_0$ is meant the absence of this radical which reverts to having a single covalent bond. (D) will preferably be a single bond or a $(CH_2)n$ group, n being an integer chosen from 1, 2 or 3.

When Ra, Rb and Rc represent a $(CH_2)_{0-3}$—Ar, $(CH_2)_{0-3}$—Het, $(CH_2)_{0-3}$—Alk group, $(CH_2)_{0-3}$ represents either a single bond in the case of $(CH_2)_0$, or —$CH_2$—, —$(CH_2)_2$— or —$(CH_2)_3$— radicals.

By the term (Ar) representing a carbocyclic aryl group containing 6 to 18 carbon atoms, is meant a radical derived from an aromatic cyclic hydrocarbon such as the phenyl, naphthyl, phenanthrenyl radical or a radical derived from a condensed bicyclic or tricyclic hydrocarbon comprising a benzene ring such as indanyl, indenyl, dihydronaphtyl, tetrahydronaphtyl or fluorenyl. The junction is carried out at the level of the benzene ring. It is preferably phenyl.

By the term (Het) representing a radical derived from an aromatic or non aromatic, saturated or non saturated heterocycle, comprising 1 to 9 carbon atoms and 1 to 5 heteroatoms chosen from oxygen, nitrogen and sulphur atoms, is designated in particular:

heterocyclic monocyclic radicals, for example thienyl, furyl, pyrannyl, pyrrolyl, imidazolyl, pyrazolyl, pyridyl, pyrazinyl, pyrimidinyl, pyridazinyl, thiazolyl, oxazolyl, furazannyl, pyrrolinyl, imidazolinyl, pyrazolinyl, thiazolinyl, triazolyl, tetrazolyl radicals, heterocyclic condensed rings, for example benzofurannyl, benzothienyl, benzimidazolyl, benzothiazolyl, naphtho [2,3-b]thienyl, thianthrenyl, isobenzofurannyl, chromenyl, xanthenyl, phenoxathiinyl, indolizinyl, isoindolyl, 3H-indolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, beta-carbolinyl, acridinyl, phenothiazinyl, phenoxazinyl, indolinyl, isoindolinyl, imidazopyridyl, imidazopyrimidinyl or also polycyclic condensed systems constituted by heterocyclic monocyclics as defined above such as for example furo[2,3-b]pyrrole or thieno[2,3-b]furan, or saturated heterocycles such as pyrrolidine, piperidine, morpholine.

This term (Het) includes moreover the values of (Het') as defined previously.

By the term (Alk) representing a radical derived from a non aromatic, linear, branched or cyclic, saturated or unsaturated hydrocarbon, is designated in the case of acyclic hydrocarbons alkyl radicals such as methyl, ethyl, propyl, isopropyl, butyl, isobutyl, tert-butyl, n-pentyl, n-hexyl, 2-methyl pentyl, 2,3-dimethyl butyl, n-heptyl, 2-methylhexyl, 2,2-dimethylpentyl, 3,3-dimethyl pentyl, 3-ethylpentyl, n-octyl, 2,2-dimethylhexyl, 3,3-dimethylhexyl, 3-methyl-3-ethylpentyl, nonyl, 2,4-dimethylheptyl or n-decyl, alkenyl radicals such as vinyl, propenyl, isopropenyl, allyl, 2-methylallyl, butenyl or isobutenyl, or alkynyl radicals such as ethynyl, propynyl, propargyl, butynyl or isobutynyl, and in the case of cyclic radicals, cycloalkyl radicals, such as cyclopropyl, cyclobutyl, cyclopentyl, cyclohexyl or adamantyl.

When Ra and Rb represent together with the nitrogen atom to which they are linked a nitrogenous heterocycle, it is in particular the following saturated heterocycles morpholine, piperidine, piperazine, pyrrolidine, or unsaturated heterocycles such as pyrimidine, pyridine or pyrazine.

When $R_2$, $R_3$, $R_4$ and $R_5$ represent an O—(Alk) radical containing 1 to 12 carbon atoms, it is preferably methoxy, ethoxy, propyloxy, isopropyloxy, butyloxy, allenyloxy or propargyloxy radicals. When $R_2$, $R_3$, $R_4$ and $R_5$ represent an O—$(CH_2)_{0-3}$—Ar radical phenylethoxy and phenylpropyloxy radicals are preferably meant.

When $R_2$ and $R_3$ form together a ring of —O—$(CRdRe)_n$—O— type, n being an integer from 1 to 5, it is in particular the —O—$CH_2$—O, O—$C(Me)_2$—O, O—$C(Ph)_2$—O, O—$C(CH_3)$ (Ph)—O radicals, $R_2$ and $R_3$ are imperatively in ortho position relative to each other.

When $R_6$ represents an O—Alk or O—Ar radical, Alk and Ar being substituted or non substituted, it is in particular the following radicals: $(C_1–C_8)$ alkoxy, $(C_1–C_{14})$-aryl $(C_1–C_8)$-alkoxy, $(C_6–C_{14})$ aryloxy, $(C_1–C_8)$ alkylcarboxyloxy, $(C_1–C_8)$ dialkylaminocarbonylmethoxy, $(C_6–C_{14})$ aryl $(C_1–C_8)$ dialkylaminocarbonylmethoxy.

When $R_6$ represents an NH—alk, NH(alk)$_2$ or NH—Ar radical, it is in particular the $(C_1–C_8)$ alkylamino, di-$(C_1–C_8)$ alkylamino, $(C_6–C_{14})$ aryl $(C_2–C_8)$ alkylamino, $(C_6–C_{14})$ arylamino radicals.

When $R_6$ represents the remainder of an amino acid it can be L or D amino acid.

The L or D amino acids can be natural or not natural. Preferably it is α-amino acids. For example, those described in Houben-Weyl, Methoden der organischen Chemie, Band XV/1 and 2, Georg Thieme Verlag, Stuttgart, 1974: Aad, Abu, γAbu, Abz, 2ABz, εAca, Ach, Acp, Adpd, Ahb, Aib, βAib, Ala, βAla, Δala, Alg, All, Ama, Amt, Ape, Apm, Apr, Arg, Asn, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hIle, hLeu, hLys, hMet, hphe, hpro, hSer, hThr, hTrp, hTyr, Hyl, Hyp, 3Hyp, Ile, Ise, Iva, Kyn, Lant, Lcn, Leu, Lsg, Lys, βLys, Δlys, Met, Mim, Min, nArg, Nle, Nva, Oly, Orn, Pan, Pec, Pen, Phe, Phg, Pic, Pro, Δpro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val, tert-butylglycine (Tbg), Neopentylglycine (Npg), Cyclohexylglycine (Chg), Cyclohexylalanine (Cha), 2-Thienylalanine (Thia), 2,2-diphenylaminoacetic acid, 2-(p-tolyl)2-phenylamino acetic acid, 2-(p-chlorophenyl) amino acetic acid, or also 2-pyrrolidine acetic acid, 1,2,3,4-tetrahydroisoquinoline 3-acetic acid, decahydroisoquinoline 3-acetic acid, octahydroisoindol 2-acetic acid, decahydroquinoline 2-acetic acid, octahydrocyclopenta[b]pyrrol 2-carboxylic acid, 2-azabicyclo[2,2,2]octan-3-carboxylic acid, 2-azabicyclo [2,2,1]heptan-3-carboxylic acid, 2-azabicyclo[3,1,0]hexan-3-carboxylic acid, 2-azaspiro[4,4]nonan-3-carboxylic acid, 2-azaspiro[4,5]decan-3-carboxylic acid, spiro (bicyclo [2,2,1]heptan)-2,3-pyrrolidin-5-carboxylic acid, spiro (bicyclo [2,2,2]octan-2,3-pyrrolidin-5-carboxylic acid, 2-azatricyclo [4,3,0,1$^{6,9}$]decan-3-carboxylic acid, decahydrocyclohepta [b]pyrrol-2-carboxylic acid, decahydrocycloocta[c]pyrrol-2-carboxylic acid, octahydrocyclopenta[c]pyrrol-2-carboxylic acid, octahydroisoindol-1-carboxylic acid, 2,3, 3a,4,6a-hexahydrocyclopenta [b]pyrrol-2-carboxylic acid, 2,3,3a,4,5,7a-hexahydroindol-2-carboxylic acid, tetrahydrothiazol-4-carboxylic acid, isoxazolidin-3-carboxylic acid, pyrazolidin-3-carboxylic acid, hydroxypyrrolidin-2-carboxylic acid, which if appropriate, can be substituted (see the following formulae):

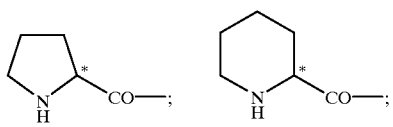

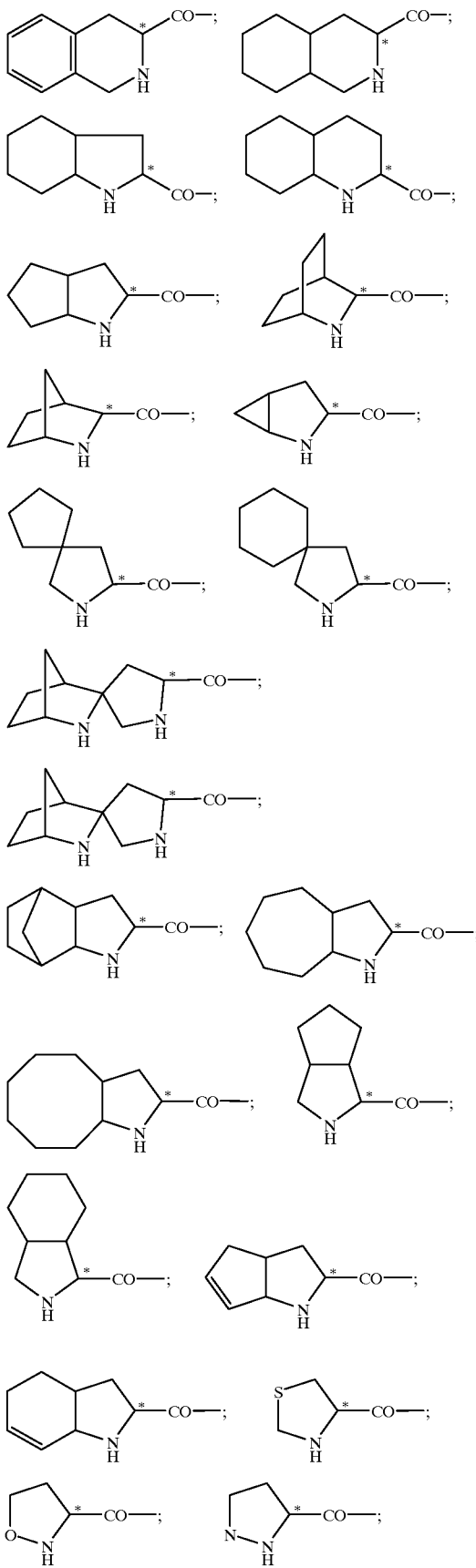

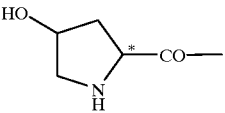

The heterocycle remainders described above are known, for example, in the following Patents or Patent Applications: U.S. Pat. No. 4,344,949; U.S. Pat. No. 4,374,847; U.S. Pat. No. 4,350,704; EP-A-29.488; EP-A-31.741; EP-A-46.953; EP-A-49.605; EP-A-49.658; EP-A-50.800; EP-A-51.020; EP-A-52.870; EP-A-79.022; EP-A-84.164; EP-A-89.637; EP-A-90.341; EP-A-90.362; EP-A-105.102; EP-A-109.020; EP-A-111.873; EP-A-271.865 and EP-A-344.682.

Moreover the amino acids can be in the form of an ester or an amide, such as for example, methyl ester, ethyl ester, isopropyl ester, isobutyl ester, tert-butyl ester, benzyl ester, ethylamide, semicarbazide or ω-amino $(C_2–C_8)$-alkylamide.

Finally, the functional groups of these amino acids can be protected. The appropriate protective groups such as the protective groups of urethanes, the protective groups of carboxyl or the protective groups of the side chains are described by Hubbuch, Kontakte (Merck)1979, No. 3, p. 14–23 and by Büllesbach, Kontakte (Merck)1980, No. 1, p. 23–35.

For example Aloc, Pyoc, Fmoc, Tcboc, Z, Boc, Ddz, Bpoc, Adoc, Msc, Moc, $Z(NO_2)$, $Z(Hal_n)$, Bobz, Iboc, Adpoc, Mboc, Acm, tertbutyl, Obzl, Onbzl, Ombzl, Bzl, Mob, Pic, Trt can be mentioned.

When G is a radical of formula G1

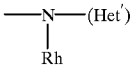

and (Het') is a heterocycle of general formula:

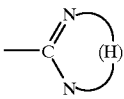

in which (H) forms, with the N=C—NH— unit, an aromatic or non aromatic, mono or bicyclic, saturated or non saturated heterocycle, comprising 1 to 9 carbon atoms and 2 to 5 heteroatoms chosen from oxygen, nitrogen and sulphur atoms, this radical being able to be substituted or non substituted, G1 represents in particular the following heterocycles:

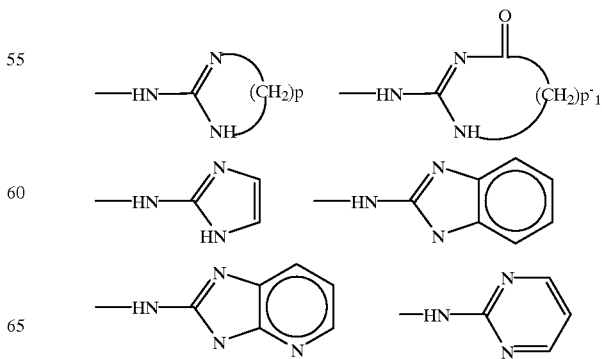

-continued

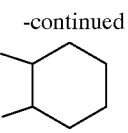

in which p represents an integer from 1 to 4.

When G is an —NRaRb radical (called G2), Ra and Rb can be a hydrogen atom, a $(CH_2)_{0-3}$—Ar, $(CH_2)_{0-3}$—Het or $(CH_2)_{0-3}$—Alk radical. The Ar, Het and Alk groups can also be substituted by the groups as defined below. G2 can be in particular an $NH_2$, NH—Alk such as NHMe, NHEt, $N(Alk)_2$ such as $NMe_2$, $NEt_2$, NMeEt, NH—$(CH_2)_{0-1}$—Ar such as NHPh, $NHCH_2Ph$ or $NHCH_2Het$ such as $NHCH_2$-pyrrol-2-yl group.

When Ra is a hydrogen atom or an (Alk) group and when Rb is a (Het') group, the values of G1 are found.

When Ra and Rb form together with the nitrogen atom to which they are linked a nitrogenous heterocycle, it is in particular the heterocyclic groups described above, these being able to be substituted or non substituted.

When G is a (Het) radical (radical G3) this radical being able to be substituted or non substituted, it is in particular the heterocycles listed above and in particular the heterocycles of general formula (Het') as defined above. When this heterocycle is linked at the level of its nitrogen atom, the values of G2 are found in which Ra and Rb form a heterocycle with the nitrogen atom which carries them.

When G is an —NRh—C(=X)—NHRc radical (radical G4), or $NRhSO_2Rc$ radical (radical G5), in which X is a sulphur, oxygen or NH atom, Rh and Rc are as defined previously. It is in particular the —NH—C(=NH)—$NH_2$, —NH—C(=O)—$NH_2$ or —NH—C(=S)—$NH_2$, —NH—C(=NH)—$NHCH_2$—Ar such as —NH—C(=NH)—$NHCH_2Ph$, —NH—C(=NH)—$NHCH_2$—Het, —NH—C(=NH)—$NHCH_2$—Het', —NH—C(=NH)—NH-Alk such as —NH—C(=NH)—$NHCH_3$, or —NH—$SO_2Ph$ groups, the Ar, Het, Het' or Alk groups being substituted or non substituted.

The optional substituents of the (Alk), (Ar), (Het), (Het') or NRaRb radicals forming a heterocycle, are preferably the following radicals:

halogen: fluorine, chlorine, bromine, iodine,
alkyl, alkenyl, alkynyl containing 1 to 12 carbon atoms such as methyl, ethyl, propyl, isopropyl, butyl, isobutyl, tert-butyl, vinyl or allenyl. These radicals being themselves optionally substituted by one or more halogen atoms, for example fluorine such as trifluoromethyl.
oxo, cyano, nitro, formyl, carboxy and carboxyalkyl containing 1 to 6 carbon atoms, carboxamide,
alkoxy containing 1 to 12 carbon atoms such as methoxy, ethoxy, propyloxy, isopropyloxy, butyloxy,
alkylthio containing 1 to 12 carbon atoms such as methylthio, ethylthio, propylthio, isopropylthio, butylthio,
amino, alkylamino containing 1 to 12 carbon atoms such as methylamino or ethylamino, dialkylamino containing 2 to 24 carbon atoms such as dimethylamino, diethylamino, methylethylamino, each of these dialkylamino radicals being optionally in oxidized form,
aminoalkyl containing 1 to 12 carbon atoms such as aminomethyl or aminoethyl,
dialkylaminoalkyl containing 3 to 25 carbon atoms such as dimethylamino methyl or ethyl,
dialkylaminoalkyloxy containing 3 to 25 carbon atoms such as dimethylaminoethyloxy,
optionally acylated hydroxyl containing 1 to 12 carbon atoms, for example acetoxy,
acyl containing 1 to 12 carbon atoms such as formyl, acetyl, propionyl, butyryl, isobutyryl, valeryl, isovaleryl, succinyl, pivaloyl benzoyl optionally substituted for example by a chlorine, iodine or fluorine atom. The chloroacetyl, dichloroacetyl, trichloroacetyl, bromoacetyl or trifluoroacetyl radicals can be mentioned,
carbocyclic or heterocyclic aryl such as phenyl, furyl, thienyl, pyridinyl or aralkyl such as benzyl, these radicals themselves being optionally substituted by the halogen, alkyl, alkoxy, alkylthio, amino alkyl or dialkylamino radicals indicated above.

When Ar represents a phenyl, this can be substituted by an O—$(CRdRe)_n$—O group as defined previously.

Of course, one or more substituents, identical or different, can be present. In the case of (Het) the substituents can be at the level of the NH group or the carbon atom.

These substituents also illustrate the definition of $R_4$.

It is of course understood that when $R_1$, $R_2$, $R_3$, $R_4$, $R_5$, $R_6$, $R_a$, $R_b$, $R_c$ represent an alkyl, aryl or heterocycle group as defined above, they can be identical or different independently of each other.

The invention naturally extends to the salts of the compounds of formula (I), such as for example the salts formed when the compounds of formula (I) comprise an amino or amino guanidine function, with the following acids: hydrochloric, hydrobromic, nitric, sulphuric, phosphoric, acetic, trifluoroacetic, formic, propionic, benzoic, maleic, fumaric, succinic, tartaric, citric, oxalic, glyoxylic, aspartic, alkanesulphonic acids such as methane or ethanesulphonic acids, arenesulphonic acids, such as benzene or paratoluene sulphonic acids and arylcarboxylic acid, or when the compounds of formula (I) comprise an acid function, with the salts of alkali or alkaline-earth metals or of ammonium optionally substituted.

The invention also extends to the esters of the compounds of formula (I).

In a first preferred group, a subject of the invention is the compounds of general formula (I) as defined previously, corresponding to general formula (I'):

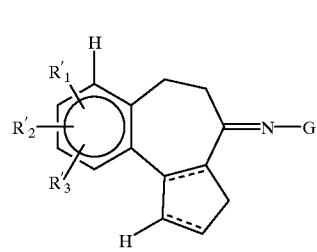

(I')

in which $R'_1$ represents a
—CONH—[A']—[B']—$COR'_6$ group, —[A']— representing a divalent alkylene, alkenylene or alkynylene radical containing 1 to 6 carbon atoms substituted by the group (Z') or non substituted, [B'] representing a CH(Z') radical or a single bond,
(Z') represents a hydrogen atom, a
$(CH_2)_{0-6}$—NRaRb, $(CH_2)_{0-6}$—NH—$SO_2$—Rc, $(CH_2)_{0-6}$—NH—$CO_2$—Rc, $(CH_2)_{0-6}$—NH—CO—Rc, $(CH_2)_{0-6}$—NH—$SO_2$—NH—Rc, $(CH_2)_{0-6}$—NH—CO—NH—Rc, $(CH_2)_{0-6}$—$CO_2$—Rc, $(CH_2)_{0-6}$—$SO_2$—Rc, $(CH_2)_{0-6}$—

CO—Rc or (CH$_2$)$_{0-6}$—Rc group, Ra, Rb and Rc being as defined previously, R'$_6$ represents an OH, amino or alkoxy radical containing 1 to 8 carbon atoms, optionally substituted by one or more radicals chosen from the hydroxy, amino, phenylalkylamino or dialkylamino radicals, R'$_2$ and R'$_3$ represent a hydrogen atom or a methoxy radical, and G is as defined previously, the dotted lines represent an optional second bond, as well as the addition salts with acids, bases and esters.

In a second preferred group, a subject of the invention is the compounds of general formula (I) as defined previously in which R$_6$ represents an —OH, —OCH$_3$, —OCH$_2$CH$_3$, —O—(CH$_2$)$_2$—OH, —O—CH$_2$—CH (OH)—CH$_2$OH, —O—(CH$_2$)$_2$—NH$_2$, —O—(CH$_2$)$_2$—N(CH$_3$)$_2$, —NH$_2$ or —O—(CH$_2$)-phenyl group, as well as the addition salts with acids, bases and esters.

In a third preferred group, a subject of the invention is the compounds of general formula (I) as defined previously in which R$_1$ represents a —CONH—CH(Z')—CH$_2$CO$_2$H or —CONH—CH$_2$—CH(Z')—CO$_2$H group, as well as the addition salts with acids, bases and esters.

In a fourth preferred group, a subject of the invention is the compounds of general formula (I) as defined previously, in which (Z') is a substituted or non substituted aryl or heteroaryl group, as well as the addition salts with acids, bases and esters.

In a fifth preferred group, a subject of the invention is the compounds of general formula (I) as defined previously, in which (Z') is the (CH$_2$)$_{0-6}$—NH—CO$_2$—Rc or (CH$_2$)$_{0-6}$—NHRb group, Rb and Rc being as defined previously, as well as the addition salts with acids, bases and esters.

In a sixth preferred group, a subject of the invention is the compounds of general formula (I) as defined previously, in which Rb and Rc represent the (CH$_2$)$_{0-3}$—Ar or (CH$_2$)$_{0-3}$—Alk groups, Ar and Alk being as defined previously and being able to be substituted or non substituted, as well as the addition salts with acids, bases and esters.

In a seventh preferred group, a subject of the invention is the compounds of general formula (I) as defined previously, in which G is a group G4 of formula —NH—C(=NH)—NHRc, Rc being as defined previously, as well as the addition salts with acids, bases and esters.

In an eighth preferred group, a subject of the invention is the compounds of general formula (I) as defined previously, in which G is a group G4 of formula NH—C(=NH)—NH$_2$, as well as the addition salts with acids, bases and esters.

In a ninth preferred group, a subject of the invention is the compounds of general formula (I) as defined previously, in which G is an —NH—(Het') group as defined previously and in particular,

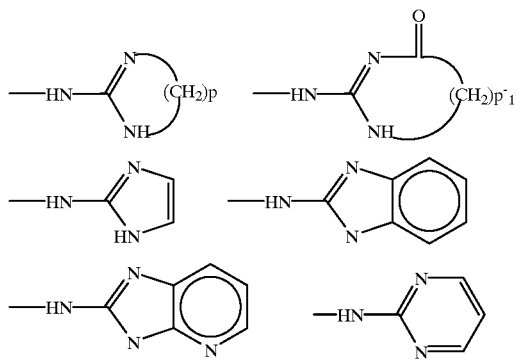

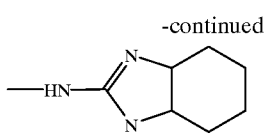

being an integer equal to 2, 3 or 4, these heterocycles being substituted or non substituted, as well as the addition salts with acids, bases and esters.

In a tenth preferred group, a subject of the invention is the compounds of general formula (I) as defined previously, in which G is the

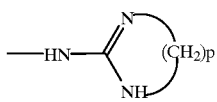

group, p being an integer equal to 2, 3 or 4, as well as the addition salts with acids, bases and esters.

In an eleventh preferred group, a subject of the invention is the compounds of formula (I) as defined previously, the names of which follow:

3-[[[4-[(4,5-dihydro-1H-imidazol-2-yl)hydrazono]-9,10-dimethoxy-1,2,3,4,5,6-hexahydro-8-benz[e]azulenyl]-carbonyl]amino]-N-[(phenylmethoxy)carbonyl]-DL-alanine 3-[[[9,10-dimethoxy-1,2,3,4,5,6-hexahydro-4-[(1,4,5,6-tetrahydropyrimidin- 2-yl)]-hydrazono]-8-benz[e] azulenyl]carbonyl]amino]-N-[(phenylmethoxy) carbonyl]-DL-alanine beta-[[[4-[(4,5-dihydro-1H-imidazol-2-yl) hydrazono]-1,2,3,4,5,6-hexahydro-8-benz[e]azulenyl]carbonyl]-amino]-3-pyridine-3-yl-propanoic acid beta-[[[4([(4,5-dihydro-1H-imidazol-2-yl) hydrazono]-(1,2,3,4,5,6-hexahydro-4-oxo-8-benz[e] azulenyl] carbonyl]-amino]-3-(1,3-benzodioxole-5-yl-propanoic acid.

A subject of the invention is also a process for the preparation of the compounds of general formula (I) comprising the following stages:

a) action of an activating agent of the alcohol function then a carbonylation reaction of the compounds of formula (II):

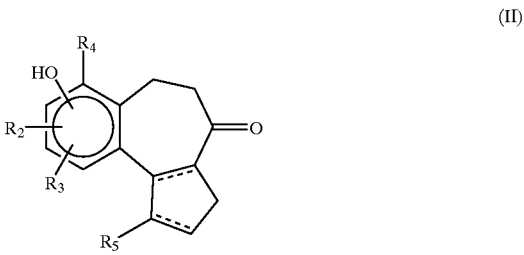

(II)

in which R$_2$, R$_3$, R$_4$ and R$_5$ are as described previously with the exception of the hydroxyl value, in order to obtain the ester of formula (IIIa):

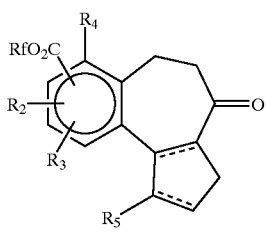

Rf being an alkyl radical containing 1 to 4 carbon atoms,
b) saponification of the ester of formula (IIIa) in order to obtain the corresponding acid of formula (IIIb):

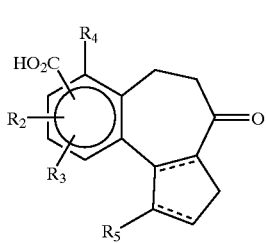

c) amidification reaction of the acid of formula (IIIb) by the action of a compound of formula (F1), if appropriate in the form of salt:

[A], [B] and $R_6$ being as defined previously, [A] or [B] can also represent the —CH—NHP group, P being a protective group of the amine function, in order to obtain a compound of formula (IIIc):

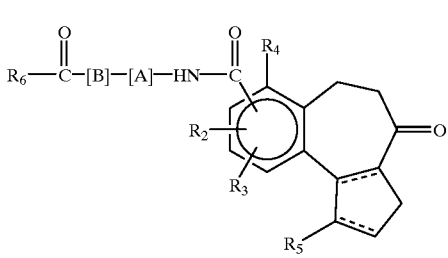

d) action on the compound of formula (IIIc) of a compound of formula (F2):

G being as defined previously, in order to obtain a compound of formula (I),
e) a compound of formula (I) which if appropriate is subjected in an appropriate order:
  to the action of a base or an acid in order to detach the ester and to obtain the corresponding acid,
  to the action of a dealkylation agent,
  to the action of a deprotection agent of the NH—P function in beta of CO—$R_6$ when [A] or [B] represents the CH—NHP group,
  to the formation of the NH—$SO_2R_c$, NH—$CO_2R_c$, NHCO$R_c$, NH—$SO_2$—NH—$R_c$, NH—CO—NH$R_c$ group the from the corresponding amine,
  to the action of an acid or a base in order to obtain the corresponding salts or to the action of an esterification agent in order to obtain the corresponding esters.

The carbonylation reaction is carried out in particular according to the method described by P. Prince, D. Richard and D. Gandour in Synlett (1991)405, and in "Palladium Reagents in Organic Synthesis" ed. Hech R. F. Academic Press N.Y. Chap. 8 (1995).

The activation of the alcohol can be carried out in particular using the triflic anhydride of formula $(CF_3SO_2)_2O$ in the presence of a base such as pyridine in order to form the corresponding triflate of formula $(OSO_2CF_3)$.

The action of the compound of formula $H_2N$—[A]—[B]—$COR_6$ (F2) preferably is carried out in basic medium, in a solvent such as dimethylformamide.

The action of $NH_2$—G (F2) is carried out, either without solvent, or in an alcoholic solvent such as ethanol, isopropanol or butanol. The synthon $NH_2$—G is optionally used in the form of a salt such as the hydrochloride or the hydrobromide.

The saponification reaction of the ester function is carried out for example by the action of an alkaline base such as soda or potash in tetrahydrofuran or a lower alcohol such as methanol or ethanol. The ester can also be detached in acid medium according to methods known to a person skilled in the art.

The dealkylation reaction allowing access to the products of formula (I) with $R_2$, $R_3$, $R_4$ or $R_5$ representing hydroxyls is carried out in the presence of aluminium chloride or boron tribromide.

The functionalization of $NH_2$, [A] or [B] representing $CH(NH_2)$ or $CH(NH_2.Hcl)$, is carried out according to the standard methods known in organic chemistry.

The formation of $NHSO_2Rc$ from the corresponding amine is preferably carried out by the action of $R_cSO_2Hal$ in the presence of a base for example triethylamine.

The formation of $NHCO_2R_c$ from the corresponding amine is preferably carried out by the action of $R_cOH$ according to the method described in J. Org. Chem., 61, 3929–3934 after having previously reacted the triphosgene in the presence of sodium bicarbonate in order to intermediately obtain the isocyanate.

The salification reactions can be carried out under the usual conditions. For example, to salify the terminal $CO_2H$ group of $R_1$, the operation is carried out in the presence of a sodium salt such as sodium carbonate or sodium or potassium acid carbonate.

Similarly, salification of the amine or the aminoguanidine which can be represented by G, with an acid, is carried out under the usual conditions. For example the operation is carried out with hydrochloric acid, for example in an ethereal solution.

The optional esterification of the products is carried out under the standard conditions known to a person skilled in the art.

In general the operation is carried out by reacting the acid of formula (I) or a functional derivative with a reagent which is capable of introducing the ester group a non-exhaustive list of which is given above in the definition of $R_6$.

The products of general formula (F1) or (F2) are known or prepared according to methods known to a person skilled in the art.

The order in which the different reagents are grafted can also be reversed, namely the compound of formula (II) is subjected to the action of compound of formula F2 in order to intermediately obtain the product of formula (IIId):

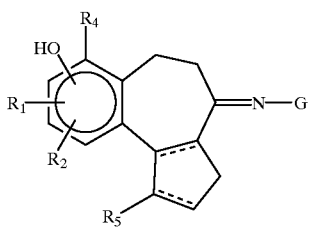

(IIId)

which is then used in the reactions as described in Stages a), b), c) and if appropriate e), in order to obtain the compounds of formula (I).

In this case, if appropriate, it will be necessary to provide protection for group G of the product of formula (IIId), then after introduction of (F1) or (F2), a deprotection according to methods known to a person skilled in the art (T. W. GREENE Protective Groups in Organic Synthesis. John Wiley and Sons Inc. 1991).

The deprotection reaction of the NH—P group in beta position of CO—$R_6$, [A] or [B] representing the CH—NHP group, is also carried out according to methods known to a person skilled in the art, in particular when P represents the $CO_2tBu$ group, by a decarboxylation reaction such as for example by the action of hydrochloric acid.

Bone is constantly subjected to a dynamic process which includes bone resorption and bone formation. These processes are mediated via specialized cells. Bone formation is the result of the deposition of a mineral matrix by the osteoblasts and bone resorption is the result of the dissolution of this bone matrix by osteoclasts. Osteoporosis is characterized by a dry loss of this bone matrix. An activated mature osteoclast resorbs the bone after adhesion to the bone matrix via the secretion of proteolytic enzymes and protons inside the adhesion zone, resulting in depressions or hollows on the bone surface which appear at the time when the osteoclast detaches itself from the bone.

The compounds of formula (I) as well as their pharmaceutically acceptable addition salts have useful pharmacological properties. These compounds inhibit bone resorption which is mediated via the osteoclasts.

The compounds of the invention are thus useful in the treatment of diseases caused by the loss of bone matrix, in particular, osteoporosis, malignancy hypercalcemia, osteopenia due to bone metastasis, parodontitis, hyperparathyroidism, the periarticular erosions in rhumatoid arthritis, Paget's disease, osteopenia induced by immobilization, treatments with glucocorticoids or male or female sex hormone deficiencies.

They can also be used for the treatment of inflammatory, cancerous and cardiovascular disorders including atherosclerosis, restenosis.

Finally, they can be used as inhibitors of angiogenesis and therefore in the treatment of tumors, by inhibition of their neovascularization, diabetic retinopathies and nephropathies.

Recent studies have shown that fixation of the osteoclast to the bone is mediated by receptors: the integrins.

Integrins are a superfamily of receptors mediating the cell/cell adhesion processes and more particularly cell/matrix, including in particular α2bβ3 as a blood platelet receptor (fibrinogen) and αvβ3 as vitronectin receptor, bone sialoproteins such as osteopontin and thrombospondin.

These receptors which are proteinic heterodimers composed of two sub-units α and β, have divalent ion fixation sites such as $Ca^{2+}$ in particular and a recognition site for their ligand predefined by the quality of their sub-units.

The αvβ3 receptor is a transmembrane glycoprotein which is expressed in a large number of cells including endothelial cells, smooth muscle cells, osteoclast and cancerous cells which thus leads to pluripotentiality of the compounds according to the invention.

The αvβ3 receptors expressed at the level of the osteoclast membrane are the basis of the adhesion/resorption process, contribute to the organisation of the cell cytoskeleton, and are involved in osteoporosis (Ross et al., J. Biol. Chem., 1987, 262, 7703).

The αvβ3 receptors expressed at the level of the smooth muscle cells of the aorta, stimulate their migration towards the neointima, which leads to the formation of atherosclerosis and the occurrence of post-angioplastic recurrence of stenosis (Brown et al, cardiovascular Res. (1994), 28, 1815).

The endothelial cells secrete growth factors which are mitogens for the endothelium and can contribute to the formation of new blood vessels (Angiogenesis). The angiogenic stimulation causes the formation of new blood vessels.

The antagonists of integrin αvβ3 can thus lead to a regression of cancerous tumors by inducing the apoptosis of the angiogenic blood vessels. (Brook et al. Cell (1994)79, 1157).

The natural ligands of integrin αvβ3 contain all the RGD unit (Arg-Gly-Asp). The peptides containing this RGD unit as well as the anti αvβ3 anti-bodies are known for their inhibitory capacity on the resorption of dentin, obstruction of the adhesion of the osteoclasts on the mineralized matrices (Horton et al. Exp. Cell. Res. (1991), 195, 368).

The peptide Echistatin isolated from snake venom also containing an RGD unit is described as an inhibitor of the adhesion of the osteoclasts to bone, and is therefore a powerful inhibitor of bone resorption in tissues cultured in vitro (Sato et al. J. Cell. Biol. (1990), 111, 1713) and in vivo in the rat (Fisher et al. Endocrinology (1993), 132, 1441).

The compounds of formula (I) as well as their pharmaceutically acceptable addition salts and their esters can have in particular an affinity vis-à-vis the receptor of vitronectin αvβ3 or vis-à-vis other integrins having vitronectin (αvβ1, αvβ5, αvβ3) for ligand by inhibiting the bond to their natural ligand.

This property thus renders the compounds of the invention of use for the prevention or the treatment of diseases the underlying pathology of which is caused by the ligands or cells which interact with the vitronectin receptor.

These compounds can also have an activity vis-à-vis other integrins which interact with their ligand via the tripeptide sequence RGD, giving them pharmacological properties which can be used for treating pathologies associated with these receptors.

This activity vis-à-vis integrins therefore renders the compounds of the invention of use in the treatment of numerous diseases such as those mentioned above or in the article by Dermot Cox DN&P 8(4) May 1995, 197–205 the content of which is included in the present Application.

Therefore a subject of the invention is the compounds of formula (I) as medicaments, as well as their pharmaceutically acceptable addition salts or their esters.

Among the medicaments according to the invention, the compounds described in the experimental part can be particularly mentioned.

Among these products, a more particular subject of the invention is, as medicaments, the compounds of formula (I) listed previously.

The dosage varies as a function of the illness to be treated and the administration route: it can vary for example from 1 mg to 1000 mg per day in an adult by oral route.

The invention extends to the pharmaceutical compositions containing at least one medicament as defined above as active ingredient.

The compounds of formula (I) are used by digestive, parenteral or local route, for example by percutaneous route. They can be prescribed in the form of plain or coated tablets, gelatin capsules, granules, suppositories, pessaries, injectable preparations, ointments, creams, gels, microspheres, nanospheres, implants, patches which are prepared according to the usual methods.

The active ingredient or ingredients can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The products of formula (II), in which the hydroxy radical is in position 10, $R_2$ in position 8 and $R_3$ in position 9, represent an O—(Alk) or O—$(CH_2)_{0-3}$—Ar group, $R_4$ and $R_5$ are hydrogen atoms, are prepared according to the method described in the European Patent Application No. 0729933 and in the International Patent Application WO 97/34865 (Preparation 2).

The two other position isomers can be prepared in the following manner:

A compound of formula (IIA):

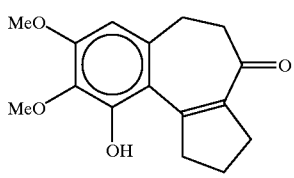
(IIA)

is subjected to the action of a dealkylation reagent, in order to obtain the compound of formula (IIB):

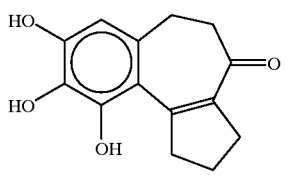
(IIB)

which compound of formula (IIB) is subjected: either to the action of a protective reagent of the diols in basic medium, in order to selectively obtain the product of formula (IIC):

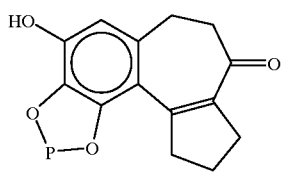
(IIC)

in which P represents the remainder of a protective reagent of the diols,
which is successively subjected to the action of a protective reagent of the phenol, of a deprotection reagent of the diols, of an alkylation agent then of a deprotection agent of the phenol in order to obtain the compound of formula (IID) corresponding to the trisubstituted product of formula (II) with OH in position 8:

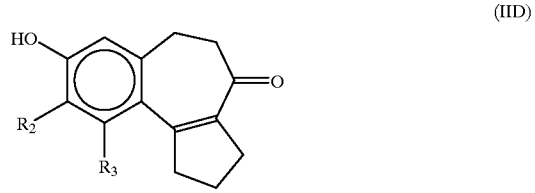
(IID)

or successively to the action of a protective agent of the phenol, of an alkylation agent then of a deprotection agent in order to obtain the compound of formula (IIE) corresponding to the trisubstituted product of formula (II) with OH in position 9

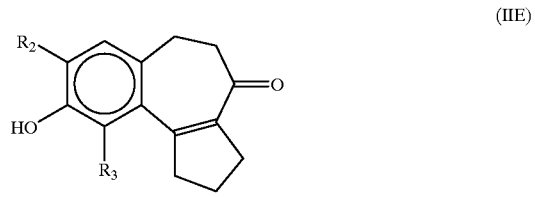
(IIE)

By dealkylation reagent, is preferably meant agents such as boron tribromide or aluminium chloride.

The protective reagent of the diols which is reacted on the products of formula (IIB) can be a boron derivative such as boric acid, a trialkyl borate, for example trimethyl or triethyl, or also borax.

By protective agent of the phenol, is meant in particular a halide such as mesyl or tosyl chloride or bromide or also a benzylated derivative such as benzyl tosylate or mesylate.

By deprotection reagent of the diols, is meant in particular a strong acid such as hydrochloric acid, sulphuric acid or paratoluene sulphonic acid or also an oxidizing agent, for example hydrogen peroxide, in the case of protection by a boron derivative.

By alkylation agent, is meant any standard agent known to a person skilled in the art for the alkylation of phenols. For example an alkyl halide such as methyl or ethyl chloride, an alkyl sulphate such as methyl or ethyl sulphate, or also diazomethane can be mentioned.

By deprotection agent, is meant a base such as soda, potash or also sodium or potassium carbonate.

The monosubstituted products of formula (II), in which $R_2$, $R_3$, $R_4$ and $R_5$ represent a hydrogen atom, are prepared according to a similar method to that described in the European Patent Application No. 0729933:

(i) a compound of formula (a):

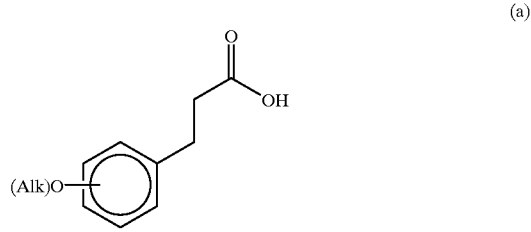
(a)

in which O—(Alk) is in meta or para position of the alkylcarboxylic group, (Alk) being as defined previously, is subjected to the action of a halogenation agent in order to obtain the corresponding acyl halide, (ii) which is subjected to the action of a reagent of formula (b):

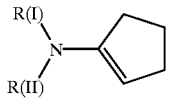
(b)

in which R(I) and R(II), identical or different represent an alkyl group containing 1 to 6 carbon atoms, or R(I) and R(II) together with the nitrogen atom to which they are linked, represent a heterocycle with 5 or 6 members, saturated or unsaturated, optionally containing another heteroatom chosen from 0 and N, in order to obtain a compound of formula (c):

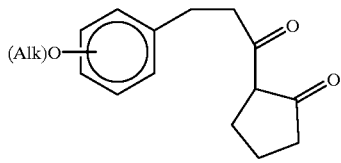
(c)

(iii) which is subjected to the action of a halogenation agent in order to obtain a compound of formula (d):

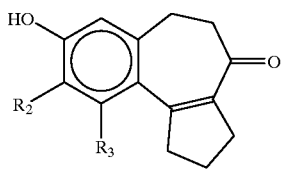
(d)

in which $Hal_1$ represents a halogen atom, (iv) which is subjected to the action of a Lewis acid, in order to obtain a compound of formula (e):

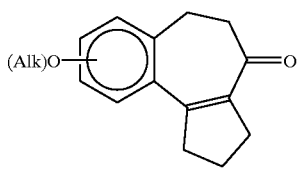
(e)

v) which is subjected to a dealkylation reagent in order to obtain the product of formula (IIF) corresponding to the expected monosubstituted product of formula (II):

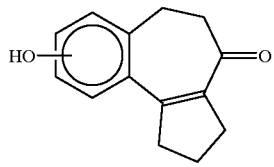
(IIF)

The disubstituted products of formula (II), in which $R_2$ represents O—(Alk) or O—$(CH_2)_{0-3}$—Ar, $R_3$, $R_4$ and $R_5$ are hydrogen atoms and OH and $R_2$ being in position 8, 9 or 10, are prepared according to the method described above starting from the compound of formula (a'):

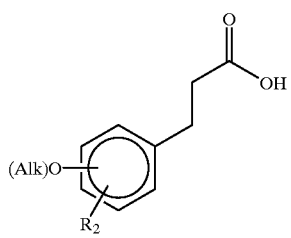
(a')

in which O—(Alk) and $R_2$ are in meta or para position of the carboxylic alkyl chain, $R_2$ being an O—(Alk) or —$(CH_2)_{0-3}$—Ar group, successively to reactions (i), (ii), (iii), (iv) and (v) and the products of formula (IIG) are obtained corresponding to the expected disubstituted products of formula (II):

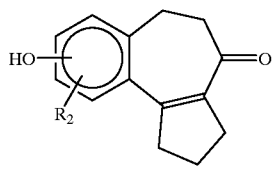
(IIG)

The halogenation agent which is reacted on the compound of formula (a) or (a') is for example thionyl chloride, oxalyl chloride or any other agent known to a person skilled in the art for preparing an acid halide.

The reagent of formula (b) is prepared starting with cyclopentanone and a secondary amine, for example diethylamine, piperidine, piperazine or, preferably, morpholine. The operation is carried out in the presence of a strong acid catalyst, for example paratoluene sulphonic acid.

The action of the enamine of formula (b) on the acid halide is preferably carried out in the presence of a tertiary amine such as triethylamine or pyridine.

The halogenation agent which is reacted on the compound of formula (c), or its disubstituted equivalent of formula (c'), can be for example thionyl chloride, phosgene, phosphorus oxychloride or, preferably, oxalyl chloride.

The Lewis acid used to cyclize the compound of formula (d), or its disubstituted equivalent of formula (d') is for example aluminium chloride, titanium tetrachloride, or preferably ferric chloride, or tin tetrachloride. The reaction, as with those above, can be carried out, for example, in a halogenated solvent such as methylene chloride, chloroform or dichloroethane.

The dealkylation reagent of the compound of formula (e), or its disubstituted equivalent of formula (e') in order to obtain the corresponding phenols is preferably aluminium chloride or boron tribromide.

The products of formula (II) in which $R_4$ is different from the hydrogen atom, are prepared by standard methods of aromatic electrophile and nucleophile substitution known to a person skilled in the art.

The products of formula (II) in which $R_5$ is different from the hydrogen atom are prepared according to methods known to a person skilled in the art and in particular according to the method described in the European Patent Application No. 0729933, i.e. by halogenation then the action of water or of an appropriate alcohol.

The products of formula (II) in which $R_5$ is a hydrogen atom and in which there is a double bond in position 1–2 are prepared according to methods known to a person skilled in the art and in particular according to the method described in the European Patent Application No. 0729933, i.e. by dehydration or dealkoxylation in an anhydrous acid medium.

The products of formula (II) in which the junction between the ring at 5 and the ring at 7 is saturated are prepared according to the standard methods of hydrogenation in particular in the presence of palladium on the carbon of the corresponding double bond.

The introduction of $R_4$, $R_5$ as well as the hydrogenation reaction is preferably carried out on the compounds of formula (IIA), (IID), (IIE), (IIF) or (IIG).

The products of formula (II) in which $R_2$ and $R_3$, in ortho position relative to each other form a ring of —O—(CRdRe)$_n$—O type as defined previously, are also prepared according to the methods known to a person skilled in the art.

A subject of the invention is also, as intermediate products, the products of formula (IIIa), (IIIb), (IIIc) and (IIId).

The following examples illustrate the invention without however limiting it.

EXAMPLE 1

3-[[[4-[(4,5-dihydro-1H-imidazol-2-yl)hydrazono]-9,10-dimethoxy-1,2,3,4,5,6-hexahydro-8-benz[e]azulenyl]-carbonyl]amino]—N-[(phenylmethoxy)carbonyl]-DL-alanine Stage A: methyl 9,10-dimethoxy-1,2,3,4,5,6-hexahydro-4-oxo-benz[e]azulene-8-carboxylate
Activation (formation of the triflate) then carbonylation 2.7 ml of anhydride triflic is added at 0–5° C. to a solution of 2.74 g of 9,10-dimethoxy-8-hydroxy-2,3,5,6-tetrahydro-benz[e]azulen-4(1H)-one prepared as indicated in Preparation 3 of the Patent Application WO 97/34865, in 20 ml of pyridine and agitation is carried out for 3 hours at this temperature. The reaction medium is poured into water, extracted, dried and evaporated under reduced pressure until 4.58 g of crude product is obtained.

1.374 g of the triflate obtained above, 84 mg of Pd(OAc)$_2$, 156 mg of 1.1'-bis(diphenylphosphino) ferrocene (Fluka), 0.82 ml of triethylamine, 9.1 ml of dimethylsuphoxide, 4.1 ml of 1,2-dichloroethane are mixed together, the reaction medium is placed under an atmosphere of CO and taken to 80° C. for 5 hours then for 16 hours at ambient temperature. The reaction medium is poured into water, extracted, dried and purified by chromatography eluting with a cyclohexane/ethyl acetate mixture.

420 mg of expected pure product is obtained.

| IR (CHCl$_3$) | |
|---|---|
| C=O | 1723 cm$^1$ methyl ester |
| | 1650 cm$^{-1}$ conjugated ketone |
| C=C + aromatic | 1587 cm$^{-1}$, 1550 cm$^{-1}$ |

Stage B: methyl 3-[[(9,10-dimethoxy-1,2,3,4,5,6-hexahydro-4-oxo-8-benz[e]azulenyl]carbonyl]amino]-N-[(phenylmethoxy)carbonyl]-DL-alaninate
Saponification (formation of the acid) then amidification 2.4 ml of 1N soda is added to 382 mg of the ester obtained in the preceding stage in 5 ml of methanol and agitation is carried out for 1 hour. After evaporation of the methanol, dilution with water and extraction with ethyl acetate, acidification is carried out to pH 1–2 with 1N hydrochloric acid, followed by extraction with ethyl acetate and drying. 348 mg of crude product is obtained.

338 mg of the acid obtained above, 10 ml of dimethylformamide, 540 mg O-(benzotriazol-1-yl)-N,N,N', N'-tetramethyluronium tetrafluoroborate (Fluka), 0.62 ml of diisopropylethylamine and 330 mg of the methyl ester of —N-α-(CO$_2$—CH$_2$-phenyl)-α, β-diaminopropionic acid, obtained according to the process described by Tamura Noribazu Chem. Pharm. Bull. 39 (5), 1199 (1991) are agitated at ambient temperature overnight under an inert atmosphere. After dilution with ethyl acetate, washing, drying and evaporation under reduced pressure 622 mg of expected product is obtained.

| IR (CHCl$_3$) | |
|---|---|
| =C—NH | 3423 cm$^{-1}$, 3376 cm$^{-1}$ |
| C=O | 1721 cm$^{-1}$, 1672 (sh), 1655 (max) cm$^{-1}$ |
| C=C + | 1625 cm$^{-1}$ |
| amide II | 1600, 1587, 1528, 1512 cm$^{-1}$ |
| NH/NH$_2$ | 1534 cm$^{-1}$, 1491 cm$^{-1}$ |

Stage C: methyl 3-[[[4-[(4,5-dihydro-1H-imidazol-2-yl)hydrazono]-9,10-dimethoxy-1,2,3,4,5,6-hexahydro-8-benz[e]azulenyl]-carbonyl]amino]-N-[(phenylmethoxy)carbonyl]-DL-alaninate
Introduction of G 300 mg of the amide obtained in Stage B, 304 mg of 2-hydrazino-2-imidazoline hydrobromide and 2.5 ml of butanol are mixed together for 16 hours at 120° C. Evaporation under reduced pressure is carried out until 600 mg of crude product is obtained which is purified by chromatography eluting with a dichloromethane/methanol/ammonium hydroxide mixture 90/10/2. 293 mg of expected pure product is obtained.

| IR (CHCl$_3$) | |
|---|---|
| —NH | 3444, 3320 cm$_{-1}$ |
| C=O | 1742 cm$^{-1}$ (sh), 1721 (max) cm$^{-1}$ |
| C=C + | 1625 cm$^{-1}$ |
| C=N | 1648 (sh), 1625, 1512 cm$^{-1}$ (max, F) |
| Conjugated system + aromatic | 1595 (sh), 1530, 1510 cm$^{-1}$ |

Stage D: 3-[[[4-[(4,5-dihydro-1H-imidazol -2-yl) hydrazono[-9,10-dimethoxy-1,2,3,4,5,6-haxahydro-8-benz[e]azulenyl]-carbonyl]amino-N-[(phenylmethoxy)carbonyl]-DL-alanine Saponification of the methyl ester 262 mg of the ester obtained in Stage C, 3 ml of methanol and 0,45 ml of 2N soda are agitated at ambient temperature for 1 hour 30 minutes.

After dilution in 5 ml of water, extraction with ethyl acetate, acidification of the aqueous phase to pH 6 with 1N hydrochloric acid, filtration and drying, 166 mg of expected pure product is obtained.

| NMR (CDCl$_3$) | |
|---|---|
| 1.86 | CH$_2$ in position 2 |
| 2.02 | |
| 2.70 to 3.85 | =C—C$\underline{H}_2$ and =N—C$\underline{H}_2$ |
| 3.61 (s), 3.68 (s), 3.75 (s) | Ph—O—C$\underline{H}_3$ |
| 4.02 (m), 4.10 | —C(O)—C$\underline{H}$—NHC(O)— |
| 5.04 (AB) | CO$_2$—C$\underline{H}_2$—Ph |
| 7.60 | aromatic H |
| 7.48 (s), 7.50 (s) | Ph-H, H in position 7 |
| 7.88 | mobile H |
| 8.44 | CON$\underline{H}$—CH$_2$ |

EXAMPLE 2

3-[[[9,10-dimethoxy-1,2,3,4,5,6-hexahydro-4-[(1,4,5,6-tetrahydropyrimidin-2-yl)]-hydrazono]-8-benz[e]azulenyl]carbonyl]amino]-N-[(phenylmethoxy)carbonyl]-DL-alanine The operation is carried out as in Example 1, Stages A, B, C and D but by using 2-hydrazino-1,4,5,6-tetrahydropyrimidine (Acros) hydrobromide as cyclic aminoguanidine.

| NMR (CDCl$_3$) | |
|---|---|
| 1.87 | central C$\underline{H}_2$'s |
| 2.40 to 3.00 | =C—C$\underline{H}_2$ |
| 3.40–3.77 | =C—N—C$\underline{H}_2$ |
| 4.20 (m) | C(O)—C$\underline{H}$—NHC(O) |
| 3.71 (s) | Ph—OMe |
| 5.04 [AB] | CO$_2$—C$\underline{H}_2$—Ph |
| ≈7.30 (m), 7.44 (bs) | aromatic H |
| 7.51 (m) | |
| 8.30 to 8.43 | mobile H |

EXAMPLE 3 beta-[[[4-[(4,5-dihydro-1H-imidazol-2-yl)hydrazono]-1,2,3,4,5,6-hexahydro-8-benz[e]azulenyl]-carbonyl]-amino]-3-pyridine-3-yl-propanoic acid Stage A: methyl 1,2,3,4,5,6-hexahydro-4-oxo-benz[e]azulene-8-carboxylate Activation (formation of the triflate) then carbonylation The operation is carried out as in Example 1, Stage A but starting from 1.3 g of 8-hydroxy-2,3,5,6-tetrahydro-benz[e]azulen-4(1H)-one prepared as indicated in Preparation 7 of the Patent Application WO 97/34865. 678 mg of expected product is obtained (M.p.=126–128° C.).

| IR (CHCl$_3$) | |
|---|---|
| C=O | 1719 cm$^{-1}$, 1645 cm$^{-1}$ |
| C=C + aromatics | 1608, 1594, 1560, 1497 cm$^{-1}$ |
| CO$_2$Me | 1438 cm$^{-1}$ |

Stage B: ethyl 3-[[(9,10-dimethoxy-1,2,3,4,5,6-hexahydro-4-oxo-8-benz[e]azulenyl]carbonyl]-amino]-3-pyridine-3-yl-propanoate Saponification of the ester then amidification The operation is carried out as in Example 1, Stage B but starting from 670 mg of the product obtained in the preceding stage and by using 0.188 g of ethyl 3-amino-3-pyridin-3-yl-propanoate hydrochloride, obtained according to the process described by Secor J. Org. Chem. N.Y., 3136–8 (1979).

271.2 mg of expected pure product is obtained.

Stage C: ethyl beta-[[[4-[(4,5-dihydro-1H-imidazol-2-yl)hydrazono]-1,2,3,4,5,6-hexahydro-8-benz[e]azulenyl]carbonyl]-amino]-3-pyridin-3-yl-propanoate acid Introduction of G The operation is carried out as in Stage C of Example 1, starting from 271.2 mg of the product obtained in the preceding stage. 93.7 mg of expected product is obtained.

| IR (CHCl$_3$) | |
|---|---|
| NH | 3452 cm$^{-1}$ |
| C=O | 1723 cm$^{-1}$ |
| C=O, C=N, | 1644, 1622 (Max, F), 1547, 1514, 1487 cm$^{-1}$ |
| C=C, aromatics | |

Stage D: beta-[[[4-[(4,5-dihydro-1H-imidazol-2-yl)hydrazono]-1,2,3,4,5,6-hexahydro-8-benz[e]azulenyl]carbonyl]-amino]- 3-pyridin-3-yl-propanoic acid Saponification of the ester The operation is carried out as in Stage D of Example 1, starting from 90 mg of the product obtained in the preceding stage.

67.6 mg of expected pure product is obtained. M.p.=218° C.
Rf CH$_2$Cl$_2$/MeOH/NH$_2$OH 40/20/2=0.25

| 1.85 (m) | CH$_2$ in position 2 |
|---|---|
| 2.65 to 3.01 10 H | =C—C$\underline{H}_2$ |
| 3.44 (s) | =N—C$\underline{H}_2$ |
| 5.42 (q) | =C—C$\underline{H}$—NHCO |
| 7.33 (m) 2H; 7.70 (m) 2H, 7.18 (m) H'$_5$; 8.46 (dd) H'$_6$; 8.60 (d) aromatic H'$_2$ | |
| 8.94 (d) | mobile H CO—N$\underline{H}$—CH |

EXAMPLE 4 beta-[[[4-[(4,5-dihydro-1H-imidazol-2-yl)hydrazono] 1,2,3,4,5,6-hexahydro-4-oxo-8-benz[e]azulenyl]-carbonyl]-amino]-3-(1,3-benzodioxole-5-yl-propanoic acid The operation is carried out as in Example 3, Stages A, B, C and D but by using in Stage B, ethyl 3-amino-3-(1,3-benzodioxol-5-yl)-propanoate hydrochloride, obtained according to the process described by A. Zablochi J. Med. Chem. 38(13)2378–2394 (1995).

| NMR (DMSO) | |
|---|---|
| 1.83 (m) | $CH_2$ in position 2 |
| 2.60 to 2.95 10 H | =C—$CH_2$ |
| 3.42 | =N—$CH_2$ |
| 5.32 (q) | C(O)—NH—C$\underline{H}$(Ph)—$CH_2$ |
| 5.96 (bs) | —O—$C\underline{H}_2$—O— |
| 6.82 [AB] | H'$_4$ and H'$_5$ |
| 6.99 (bs) | H'$_7$ |
| 7.65 (bs) | H aromatic H in position 7 |
| 7.35 (d) | H aromatic H in position 10 |
| 7.69 (d) | H aromatic H in position 9 |
| 8.78 (d) | =C—N$\underline{H}$—CH |

Pharmaceutical compositions

Tablets were prepared corresponding to the following formula:

| | |
|---|---|
| product of Example 1 | 50 mg |
| Excipient (talc, starch, magnesium stearate) | 120 mg |
| QS for a tablet completed at | |

PHARMACOLOGICAL STUDY OF THE PRODUCTS OF THE INVENTION

1—Study by the Products of the Invention of the Bond Displacement: Vitronectin/Vitronectin Receptor ($\alpha_v\beta_3$)

Protocol:

96-well MaxiSorp plates are coated overnight at 4° C., with 100 µl of human Vitronectin (cf Yatohgo et al. Cell., Structure and fraction 13: 281–292 (1988)) at 2 µg/ml, (Dilution in coating buffer).

The next day, the wells are emptied and the ligands (Vitronectin) are then fixed (see fixation buffer) for 1 hour at ambient temperature under gentle agitation.

The wells are washed six times (see washing buffer), then the following are added per well and in this order:

40 µl of incubation buffer,

10 µl of the dilution of the product to be tested, (the products are diluted in a 50/50 mixture of DMSO—$H_2O$)

50 µl of human $\alpha_v\beta_3$ receptor (cf Pytela et al. Methods Enzymol (1987)144:475) (dilution in incubation buffer, adapted according to the batch of receptor and according to the ligand).

The ligand, the human $\alpha_v\beta_3$ receptor and the products to be studied are incubated for 3 hours at ambient temperature under gentle agitation.

The wells are again washed six times, then incubated for 2 hours at ambient temperature under gentle agitation, in the presence of 100 µl of 4B12-HRP antibody, anti-receptor coupled to a peroxidase (the 4B12-HRP antibody is diluted in incubation buffer. The dilution is adapted according to the batch of receptor).

The wells are then washed six times before measurement of ligand-receptor bond is carried out using a peroxidase developer kit (TMB Microwell Peroxidase Substrate System Kirkegaard: Ref. cat. 50-76-00).

This kit contains a flask A of substrate (3,3',5,5'-tetramethylbenzidine at 0.4 g/l) and a flask B ($H_2O_2$ at 0.02% in Citrate/Citric acid buffer). Extemporaneously, one volume of A is mixture with one volume of B, then the reaction mixture is distributed at the rate of 100 µl/well. The enzymatic reaction develops in 12' for Vitronectin/$\alpha_v\beta_3$, then its development is stopped by the addition of 100 µl of 1M phosphoric acid.

The optical density is measured at 450 nm.

Buffers:

coating buffer: 0.05 M Carbonate, NaOH pH 9.6 fixation buffer: PBS containing 0.5% of BSA (pH 7.4)

washing buffer: PBS containing 0.05% of Tween 20 (pH 7.4)

incubation buffer:
50 mM TRIS pH 7.4
0.5% BSA
0.05% Tween 20
1 mM $MnCl_2$
50 µM $CaCl_2$
50 µM $MgCl_2$
100 mM NaCl.

Expression of the results:

The following curve is plotted: the percentage of bond of human vitronectin as a function of the logarithm of the concentration of each product tested.

For each product the $IC_{50}$ is determined according to the following formula:

$$IC_{50}=(BO+Bmin)/2$$

BO=Maximum bond in the absence of any product Bmin=Minimum bond in the presence of the highest concentration of product.

| RESULTS: | |
|---|---|
| Examples | Binding competition test Vn/VR (($\alpha_v\beta_3$)) $IC_{50}$ in µM |
| EX. 1 | 0.016 |
| EX. 2 | 0.019 |
| EX. 3 | 0.10 |
| EX. 4 | 0.062 |

What is claimed is:

1. A compound selected from the group consisting of a compound of the formula

I wherein $R_1$ is —CONH—A—B—$COR_6$, A is a divalent, optionally unsaturated hydrocarbon of 1 to 12 carbon atoms unsubstituted or substituted by Z, B is selected from the group consisting of phenylene, a single bond and —CHZ—, Z is selected from the group consisting of hydrogen, —$D_{0-6}$—NH—$R_a$—$R_b$, —$D_{0-6}$—NH—$SO_2$—$R_c$, —$D_{0-6}$—NH—$CO_2$—$R_c$, —$D_{0-6}$—NH—CO—$R_c$, —$D_{0-6}$—NH—$SO_2$—NH—$R_c$, —$D_{0-6}$NH—CO—NH—$R_c$, —D—$_{0-6}$—$CO_2$—$R_c$, —$D_{0-6}$—$SO_2$—$R_c$, —$D_{0-6}$—CO—$R_c$ and —$D_{0-6}$—Rc, D is a divalent, optionally unsaturated hydrocarbon of 0 to 6 carbon atoms, $R_a$, $R_b$ and $R_c$ are individually selected from the group consisting of hydrogen, —(CH$_2$)$_{0-3}$—Ar, —(CH$_2$)$_{0-3}$—Alk and —(CH$_2$)$_{0-3}$—Het, Ar is carbocyclic aryl of 6 to 18 carbon atoms, Het is saturated or unsaturated, aromatic or non-aromatic heterocycle of 1 to 9 carbon atoms and 1 to 5 heteroatoms selected from the group consisting of oxygen, sulfur and nitrogen, Alk is saturated or unsaturated alkyl and cycloalkyl of up to 12 carbon atoms, the Ar, Alk and Het being optionally substituted or R$_a$ and R$_b$ together with the nitrogen to which they are attached form an aromatic or non-aromatic, saturated or unsaturated, optionally substituted heterocycle optionally containing at least one further heteroatom selected from the group consisting of oxygen, sulfur and nitrogen, R$_6$ is selected from the group consisting of —OH, —OAlk, —OAr, —NH$_2$, —NHAlk, —N(Alk)$_2$ and acyl of an L- or D-amino acid, R$_2$ and R$_3$ are individually selected from the group consisting of hydrogen, —OH, —OAlk and —O—(CH$_2$)$_{0-3}$—Ar or R$_2$ and R$_3$ form a ring —O—(CR$_d$R$_e$)$_n$—O—, n is an integer from 1 to 5, R$_d$ and R$_e$ are individually selected from the group consisting of hydrogen, alkyl of 1 to 6 carbon atoms and phenyl, R$_4$ is selected from the group consisting of hydrogen, halogen, —OH, —NH$_2$, —NO$_2$, —CN, acyl and acyloxy of an organic carboxylic acid of 1 to 12 carbon atoms and alkyl, alkenyl, alkynyl, alkylthio, alkoxy, alkylamino, dialkylamino, dialkylaminoalkyl and dialkylaminoalkoxy, all of up to 6 carbon atoms, R$_5$ is selected from the group consisting of hydrogen, —OH, halogen, —Alk and —O—(CH$_2$)$_{0-3}$—Ar, G is selected from the group consisting of

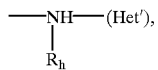

—NR$_a$R$_b$, —Het,

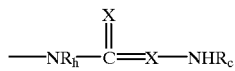

and —NR$_h$—SO$_2$—R$_c$, R$_h$ is hydrogen, or Alk, Het' is

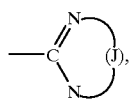

(J) is the remainder of an aromatic or non-aromatic, saturated or unsaturated, mono or bicyclic, optionally substituted heterocycle of 1 to 9 carbon atoms and 2 to 5 heteroatoms selected from the group consisting of oxygen, sulfur and nitrogen, X is selected from the group consisting of O=, S= and =NH, the dotted lines are an optional second bond, R$_1$, R$_2$ and R$_3$ are in 8, 9 or 10 position of the tricycle and its salts with non-toxic, pharmaceutically acceptable acids and bases.

2. A compound of a formula selected from the group consisting of

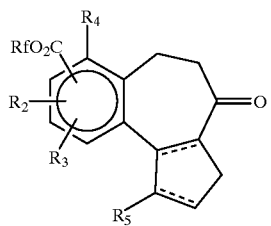

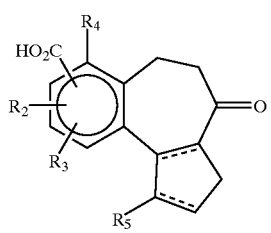

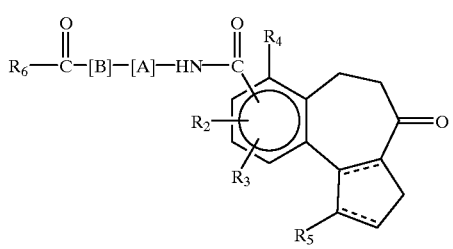

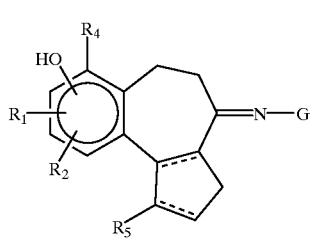

wherein R$_1$, R$_2$, R$_3$, R$_4$, R$_5$, R$_6$, A, B and G are as defined in claim 1 and R$_f$ is alkyl of 1 to 4 carbon atoms.

3. A compound of claim 1 of the formula

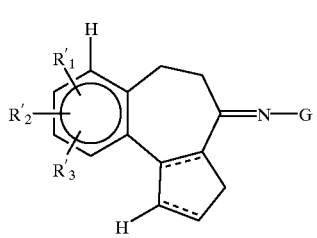

wherein R' is —CONH—A'—B'—COR'$_6$, A' is alkylene, alkenylene or alkynylene of up to 6 carbon atoms optionally substituted with Z', B' is —CH(Z') or a single bond, Z' is selected from the group consisting of hydrogen, —(CH$_2$)$_{0-6}$—NR$_a$R$_b$, —(CH$_2$)$_{0-6}$—NH—SO$_2$—R$_c$, —(CH$_2$)$_{0-6}$—NH—CO—R$_c$, —(CH$_2$)$_{0-6}$—COR$_c$ and —(CH$_2$)$_{0-6}$—Rc, R$_a$, R$_b$, R$_c$ and G defined as in claim 1, R'$_6$ is selected from the group consisting of hydrogen, —NH$_2$ and alkoxy of 1 to 6 carbon atoms unsubstituted or substituted by at least one member of the group consisting of —OH, —NH$_2$, phenylalkylamino of 1 to 6 alkyl carbon atoms and dialkylamino of 1 to 6 alkyl carbon atoms, $R'_2$ and $R'_3$ are individually hydrogen or methoxy and the dotted lines are an optional double bond.

4. A compound of claim 1 wherein $R_6$ is selected from the group consisting of —OH, —OCH$_3$, —OCH$_2$CH$_3$, —O—CH$_2$—CH$_2$—OH,

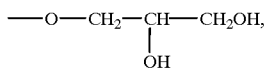

—OCH$_2$CH$_2$—NH$_2$,

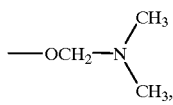

—NH$_2$ and —OCH$_2$-phenyl.

5. A compound of claim 1 wherein $R_1$ is selected from the group consisting of —CONH—CHZ'—CH$_2$—COOH and —CONH—CH$_2$—CHZ'—COOH and Z' is selected from the group consisting of hydrogen, —(CH$_2$)$_{0-6}$—NR$_a$R$_b$, —(CH$_2$)$_{0-6}$—NH—SO$_2$-R$_c$, —(CH$_2$)$_{0-6}$—NH—CO—R$_c$, —(CH$_2$)$_{0-6}$—COR$_c$ and —(CH$_2$)$_{0-6}$—Rc, R$_a$, R$_b$, R$_c$, and G defined as in claim 1.

6. A compound of claim wherein G is

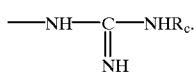

7. A compound of claim 1 wherein G is —NH—Het'.

8. A compound of claim 1 selected from the group consisting of

3-[[[4-[(4,5-dihydro-1H-imidazol-2-yl)hydrazono]-9,10-dimethoxy-dimethoxy-1,2,3,4,5,6-hexahydro-8-benz(e]azulenyl]-carbonyl]amino]-N-[(phenylmethoxy) carbonyl]-DL-alanine 3-[[[9,10-dimethoxy-1,2,3,4,5,6-hexahydro-4-[(1,4,5,6-tetrahydropyrimidin-2-yl)]-hydrazono]-8-benz[e] azulenyl]carbonyl]amino-N-[(phenylmethoxy) carbonyl]-DL-alanine beta-[[[4-[(4,5-dihydro-1H-imidazol-2-yl) hydrazono]-1,2,3,4,5,6-hexahydro-8-benz[e]azulenyl]carbonyl]-amino]-3-pyridine-3-yl-propanoic acid and beta-[[[4-((4,5-dihydro-1H-imidazo-2-yl) hydrazono]-1,2,3,4,5,6-hexahydro-4-oxo-8-benz[e)azulenyl] carbonyl]-amino]-3-(1,3-benzodioxole-5-yl-propanoic acid.

9. A compound of claim 5 herein Z' is unsubstituted or substituted aryl or heteroaryl.

10. A compound of claim 5 wherein Z' is —(CH$_2$)$_{0-6}$—NHCO$_2$—R$_c$, or —(CH$_2$)$_{0-6}$—NHR$_b$ wherein R$_b$ and R$_c$, are defined as in claim 5.

11. A compound of claim 6 wherein R$_c$ is hydrogen.

12. A compound of claim 7 wherein G is selected from the group consisting of

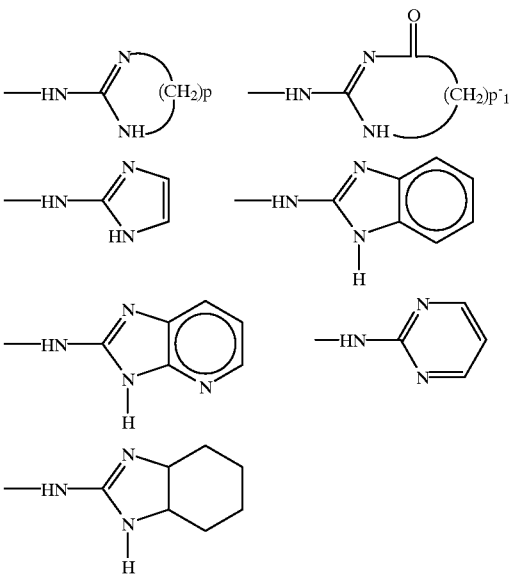

p is 2, 3 or 4, these heterocycles being substituted or non substituted, and the addition salts with pharmaceutically acceptable acids and bases thereof.

13. A compound of claim 12 wherein G is

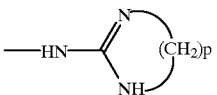

p is 2, 3 or 4, and the addition salts with acids and bases.

14. A compound of claim 10 wherein $R_b$ and $R_c$ are —(CH$_2$)$_{0-3}$—Ar or —(CH$_2$)$_{0-3}$—Alk.

15. A composition for treating loss of bone matrix comprising an effective amount of a compound of claim 1 to treat loss of bone matrix and an inert pharmaceutical carrier.

16. A composition for treating diseases caused by loss of bone matrix comprising an effective amount of a compound of claim 8 to treat loss of bone matrix and an inert pharmaceutical carrier.

17. A method of treating loss of bone matrix in warm-blooded animals comprising administering to warm-blooded animals in need thereof an amount of a compound of claim 1 sufficient to prevent loss of bone matrix.

18. A method of treating loss of bone matrix in warm-blooded animals comprising administering to warm-blooded animals in need thereof an amount of a compound of claim 8 sufficient to prevent loss of bone matrix.

19. A process for the preparation of a compound of claim 1 comprising a) reacting an activating agent of the alcohol function then carbonylating the compounds of the formula (II)

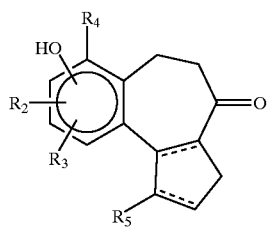

in which $R_2$, $R_3$, $R_4$ and $R_5$ are as defined in claim 1 with the exception of hydroxyl, to obtain an ester of the formula (IIIa)

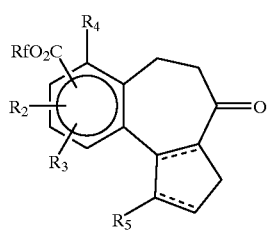

Rf is alkyl of 1 to 4 carbon atoms, b) saponificating the ester of formula (IIIa) to obtain the corresponding acid of the formula (IIIb)

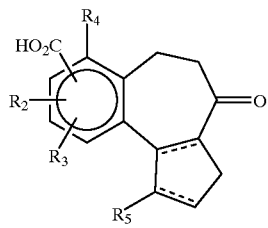

c) amidifying the acid of formula (IIIb) with a compound of the formula $$H_2N-[A]-[B]-COR_6 \quad (F1)$$

optionally in its salt form [A], [B] and $R_6$ being as defined in claim 1, [A] or [B] can also be —CH—NHP, P being a protective group of the amine function, to obtain a compound of the formula (IIIc)

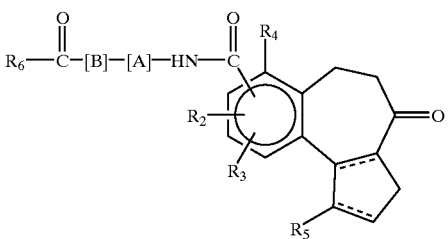

d) reacting the compound of formula (IIIc) with a compound of the formula $$G-NH_2 \quad (F2)$$

G being as defined in claim 1, to obtain a compound of formula (I), e) reacting a compound of formula (I) where appropriate in an appropriate order:
to the action of a base or an acid to detach the ester and to obtain the corresponding acid,
to the action of a dealkylation agent,
to the action of a deprotection agent of the NH—P function in beta of CO—$R_6$ when [A] or [B] is CH—NHP,
to the formation of NH—$SO_2R_c$, NH—$CO_2R_c$, NHCO$R_c$, NH—$SO_2$—NH—$R_c$, NH—CO— NHR$_c$ from the corresponding amine,
to the action of an acid or a base to obtain the corresponding salts or
to the action of an esterification to obtain the corresponding esters.

20. The process of claim 19 wherein the compound of formula (II) is subjected beforehand to the action of a compound of the formula GNH$_2$ to obtain a compound of the formula (IIId)

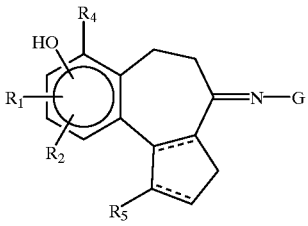

which compound of formula (IIId) is then used in the reactions as described in stages a), b), c) and optionally e).

* * * * *